United States Patent [19]

Aldrich et al.

[11] Patent Number: 4,870,186

[45] Date of Patent: Sep. 26, 1989

[54] TETRAZOLE INTERMEDIATES TO ANTIHYPERTENSIVE COMPOUNDS

[75] Inventors: Paul E. Aldrich, Wilmington; John J. V. Duncia, Newark; Michael E. Pierce, Wilmington, all of Del.

[73] Assignee: E. I. Du Pont de Nemours and Company, Wilmington, Del.

[21] Appl. No.: 275,582

[22] Filed: Nov. 23, 1988

Related U.S. Application Data

[62] Division of Ser. No. 53,198, May 22, 1987, Pat. No. 4,820,843.

[51] Int. Cl.$^4$ .................. C07D 403/14; C07D 413/14
[52] U.S. Cl. ...................................... 548/215; 548/253
[58] Field of Search ............................... 548/215, 253

[56] References Cited

PUBLICATIONS

Sisido et al., J. Organometallic Chem., 33, 337 (1971).
Sisido et al., J. Organometallic Chem., 93, 303 (1975).
Finnegan et al., J.A.C.S., 80, 3909 (1958).
Kreutzer et al., Chem. Ber., 116, 2691 (1983).

Primary Examiner—David B. Springer

[57] ABSTRACT

Tetrazole intermediates useful to prepare antihypertensive compounds described in coassigned application U.S. Ser. No. 884,920, filed July 11, 1986, are described, these tetrazoles have the formula:

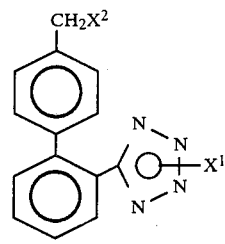

wherein $X^1$ and $X^2$ are as described in the specification.

5 Claims, No Drawings

TETRAZOLE INTERMEDIATES TO ANTIHYPERTENSIVE COMPOUNDS

This is a division of application Ser. No. 053,198, filed May 22, 1987, 4,820,843.

BACKGROUND OF THE INVENTION

1. Field of the Invention

This invention relates to substituted tetrazoles useful as intermediates in the preparation of antihypertensive compounds described in copending U.S. patent application, Ser. No. 884,920 Filed July 11, 1986.

S. Kozima et al., *J. Organometallic Chem.*, 33, 337, (1971) and ibid, 92, 303 (1975) describes substituted tetrazoles of the formula:

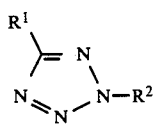

wherein $R^1$ is lower alkyl, benzyl, lower alkenyl or phenyl optionally substituted by nitro, lower alkyl, lower alkoxy or halogen; and $R^2$ is $SnR_3$.

R. Lofquist et al., *J. Amer. Chem. Soc.*, 80, 3909 (1958) describes substituted tetrazoles of the Formula:

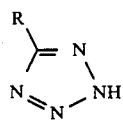

wherein

R is lower alkyl, benzyl, cycloalkyl of 4 carbon atoms, n-heptyl perfluoro, $-SR^1$ where $R^1$ is lower alkyl, benzyl; $-(CH_2)_nR^2$ where $R^2$ is OH, $CO_2R^1$, $OR^1$, $SO_3Na$ and n is 1 or 2; or phenyl optionally substituted with amino, lower alkoxy, lower alkyl, nitro or cyano.

W. Beck, et al., *Chem. Ber.*, 116, 2691 (1983) describes the preparation of 2-trityl-5-phenyl tetrazole.

SUMMARY OF THE INVENTION

According to the present invention, there are provided novel compounds of Formula (I) which are tetrazole intermediates useful for the preparation of antihypertensive compounds. These tetrazoles have the Formula:

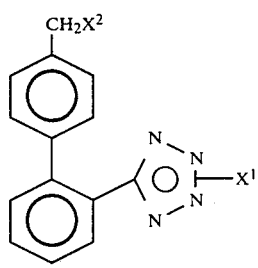

wherein $X^1$ is H, $Sn(R)_3$, $-C(Phenyl)_3$, p-nitrobenzyl, or β-propionitrile;

$X^2$ is H, Cl, Br, I, O-tosyl, OH, O-mesyl, or

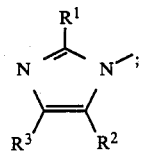

R is alkyl of 1–6 carbon atoms, phenyl or cyclohexyl;

$R^1$ is alkyl of 3–10 carbon atoms, alkenyl of 3 to 10 carbon atoms, alkynyl of 3 to 10 carbon atoms, and benzyl substituted with up to two groups selected from alkoxy of 1 to 4 carbon atoms, halogen, alkyl of 1 to 4 carbon atoms, nitro and amino;

$R^2$ is phenylalkenyl wherein the aliphatic portion is 2 to 4 carbon atoms, $-(CH_2)_m-$imidazoyl-1-yl, $-(CH_2)_m$-1,2,3-triazolyl optionally substituted with one or two groups selected from $CO_2CH_3$ and alkyl of 1 to 4 carbon atoms, $(CH_2)_m$-tetrazolyl,

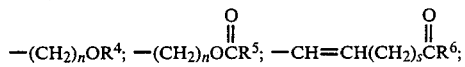

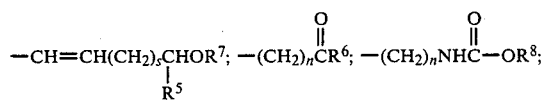

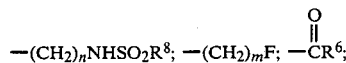

$R^3$ is H, F, Cl, Br, I, $NO_2$, $CF_3$, or CN;

$R^4$ is H, alkyl of 1 to 6 carbon atoms, cycloalkyl of 3 to 6 carbon atoms, phenyl or benzyl;

$R^5$ is H, alkyl or perfluoroalkyl of 1 to 8 carbon atoms, cycloalkyl of 3 to 6 carbon atoms, phenyl or benzyl;

$R^6$ is H, alkyl of 1–5 carbon atoms, $OR^9$ or $NR^{10}R^{11}$;

$R^7$ is H, alkyl of 1 to 6 carbon atoms, cycloalkyl of 3 to 6 carbon atoms, phenyl, benzyl, acyl of 1 to 4 carbon atoms, phenacyl;

$R^8$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^9$ is H, alkyl of 1 to 6 carbon atoms, cycloalkyl of 3 to 6 carbon atoms, or phenyl;

$R^{10}$ and $R^{11}$ independently are H, alkyl of 1 to 4 carbon atoms, phenyl, benzyl or taken together to form a ring of the Formula

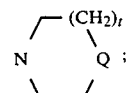

Q is $NR^{12}$, O, or $CH_2$;

$R^{12}$ is H, alkyl of 1 to 4 carbon atoms, or phenyl;

m is 1 to 5;

n is 1 to 10;

s is 0 to 5;

p is 0 to 3;

t is 0 or 1.

with the proviso that when $X^1=H$ then $X^2$ cannot be

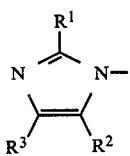

Preferred compounds are those of Formula (I) where:
X$^1$ is H, Sn(R)$_3$ or —C(phenyl)$_3$ where R is alkyl of 1 to 6 carbon atoms or phenyl; or
X$^2$ is H, Br, Cl, or the substituted imidazole; or
R$^1$ is alkyl, alkenyl or alkynyl of 3 to 7 carbon atoms;
R$^2$ is

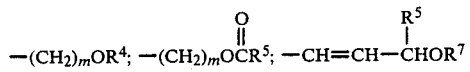

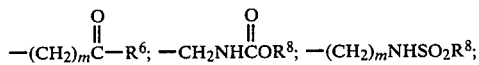

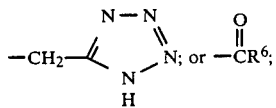

R$^3$ is H, Cl, Br, or I;
R$^4$ is H, or alkyl of 1 to 4 carbon atoms;
R$^5$ is H, or alkyl of 1 to 4 carbon atoms;
R$^6$ is H, alkyl of 1 to 5 carbon atoms; OR$^9$; or N O;
R$^7$ is H, alkyl of 1 to 4 carbon atoms, or acyl of 1 to 4 carbon atoms;
R$^8$ is CF$_3$, alkyl of 1 to 6 carbon atoms or phenyl;
m is 1 to 5.

Specifically preferred compounds are those of Formula (I) where:
(1) X$^1$ is Sn(CH$_3$)$_3$, Sn(Ph)$_3$, Sn(u-Bu)$_3$, C(Phenyl)$_3$, or H; and
X$^2$ is H or Br.
(2) X$^1$ is Sn(CH$_3$)$_3$ or C(Phenyl)$_3$; and
X$^2$ is

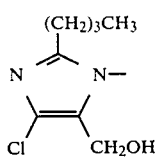

Synthesis

The novel compounds of Formula (I) may be prepared using the reactions and techniques described in this action. The reactions are performed in a solvent appropriate to the reagents and materials employed and suitable for the tranformation being effected. It is understood by those skilled in the art of organic synthesis that the functionality present on the imidazole and other portions of the molecule must be consistent with the chemical transformations proposed. This will frequently necessitate judgment as to the order of synthetic steps, protecting groups required, deprotection conditions, and activation of a benzylic position to enable attachment to nitrogen on the imidazole nucleus. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods must then be used.

Compounds of the Formula (I), here X$^1$ is Sn(R)$_3$ and R is alkyl of 1 to 6 carbon atoms or phenyl and X$^2$ is H or imidazolyl where R$^1$ is n-butyl, R$^3$ is Cl, and R$^2$ is hydroxymethyl may be prepared by the 1,3-dipolar cycloaddition of trialkyltin or triphenyltin azides to the appropriate substituted nitrile (II) (Scheme I). An example of this technique is described by S. Kozima, et al., *J. Organometallic Chemistry*, 33, 337 (1971). The nitrile (II) is described in the coassigned application U.S. Ser. No. 884,920, filed July 11, 1986. Other required nitriles and trialkyl or triaryl tin azides are either available commercially, or may be prepared using techniques and methods reported in the chemical literature, J. Luijten et al., *Rec. Trav. Chem.*, 81, 202 (1962).

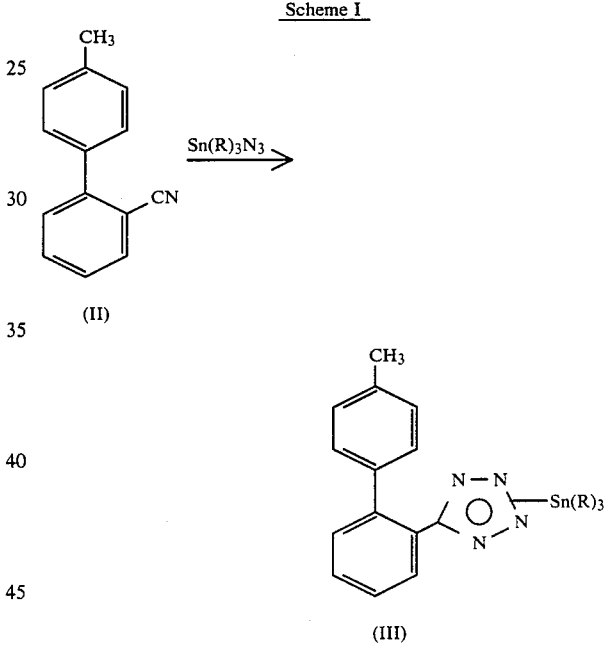

Scheme I

Compounds of the Formula (I), where X$^1$ and X$^2$ are H may be prepared by removal of a suitable protecting group on the tetrazole nucleus. Suitable protecting groups for the tetrazole moiety include p-nitrobenzyl, β-propionitrile, triphenylmethyl, and trialkyltin which are prepared via the following methods. The nitrobenzyl protecting group is attached as shown in Scheme II. The acid (IV) is converted to the intermediate acid chloride with oxalyl chloride under standard conditions. The acid chloride is converted to the amide (V) by condensation with 4-nitrobenzylamine hydrochloride in pyridine in the presence of a catalytic amount of 4-dimethylaminopyridine (DMAP). The amide (V) is converted to the intermediate iminoylchloride via reaction with phosphorus pentachloride in carbon tetrachloride. One example of this method is described by H. Ulrich, *The Chemistry of Imidoyl Halides*, Plenum Press, N.Y., N.Y. (1969). The intermediate iminoyl chloride is converted to the tetrazole (VI) with lithium azide in dimethylformamide (DMF). An example of this method is described by Elderfield, *Heterocyclic Compounds*, John Wiley and Sons, (1967). The protected tetrazole (VI) is then hydrogenated at 50 psi in the presence of a catalytic amount of W6 Raney nickel in ethanol to yield (I). The required acid (IV) is available commercially or may be prepared using techniques and methods reported in the chemical literature.

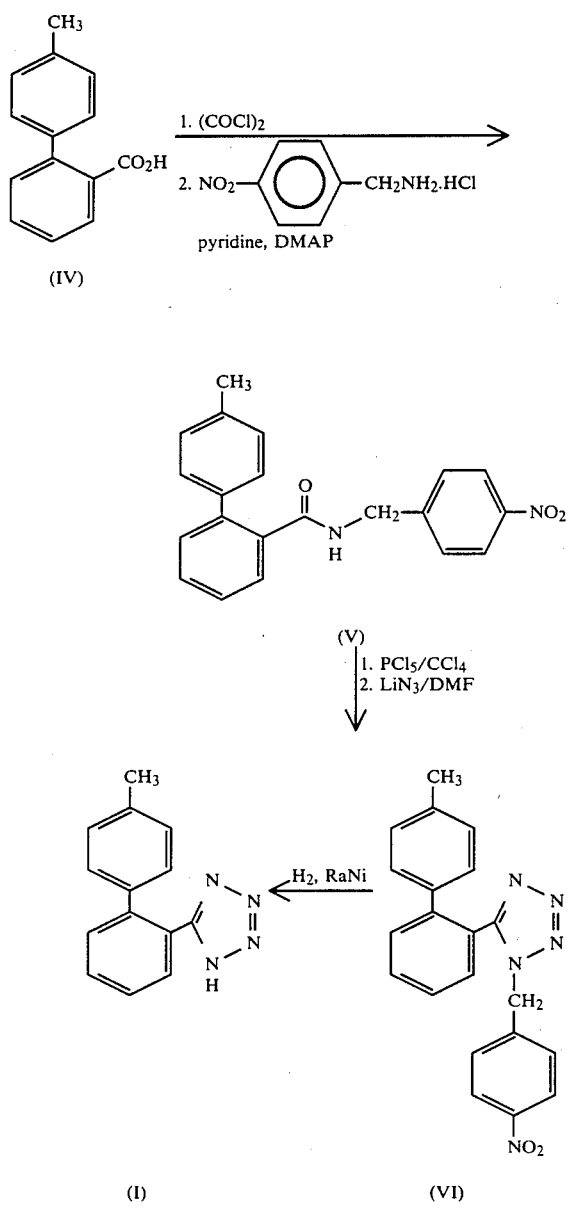

The triphenylmethyl group is attached as shown in Scheme III. The tetrazole (I) reacts with triphenylmethylchloride in methylene chloride containing triethylamine as the base under standard conditions to yield the protected tetrazole (VII).

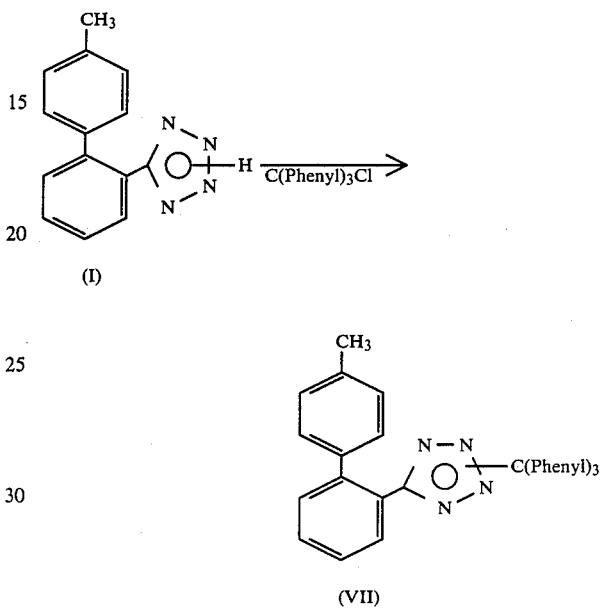

The propionitrile protecting group is attached as shown on Scheme IV. The biphenylcarboxylic acid (IV) may be converted to the acid chloride by a variety of reagents familar to one skilled in the art. The intermediate acid chloride reacts with β-aminopropionitrile in the presence of an acid scavenger such as aqueous sodium hydroxide to yield amide (VIII). Amide (VIII) reacts with phosphorus pentachloride or phosgene to form the intermediate iminoyl chloride (IX) which when reacted with hydrazine yields amidrazone (X). The amidrazone (X) reacts readily with dinitrogen tetroxide ($N_2O_4$), which can be conveniently handled as a solution in carbon tetrachloride, to yield tetrazole (XI). Hydrazines and hydrazides have been shown to undergo facile conversion to their corresponding azides with $N_2O_4$ as described by Y. H. Kim, et. al., *Tetrahedron Letters*, 27, 4749 (1986). The protected tetrazole (XI) is deprotected with aqueous base such as 1N NaOH with or without an additional organic solvent such as tetrahydrofuran to yield tetrazole (I). The amidrazone (X) may also be converted to the tetrazole (XI) using nitrous acid or its equivalents as described by D. G. Neilson, et. al., *Chem. Rev.*, 70, 151 (1970).

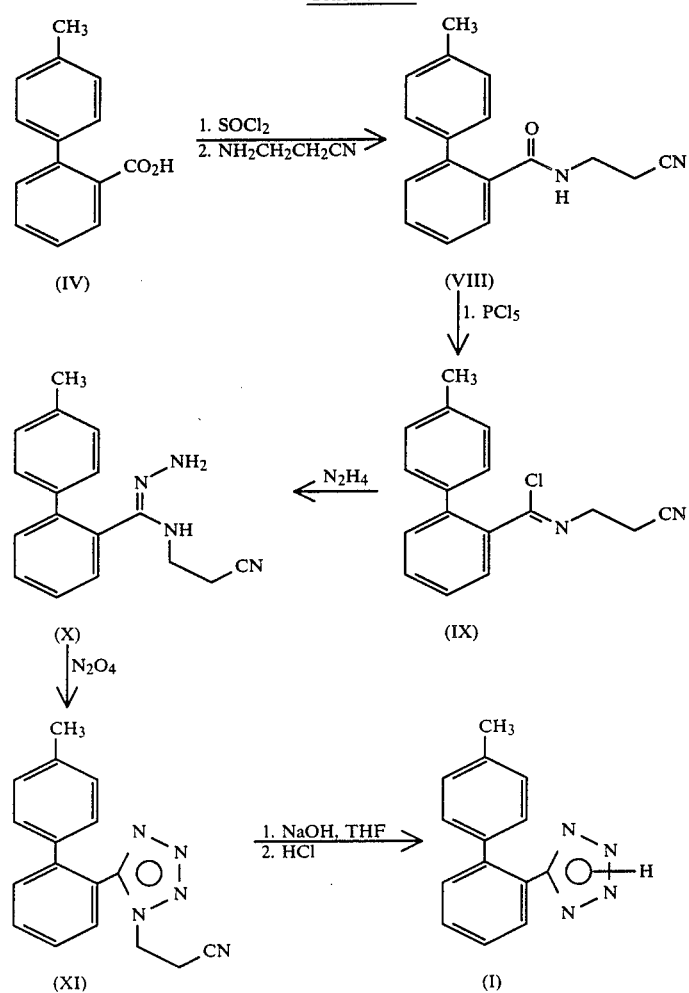
Preferred protecting groups are those where $X^1$ is $Sn(R)_3$ and $C(Phenyl)_3$ and R is as described previously (Scheme V). The above groups may be optionally removed via acidic or basic hydrolysis, catalytic hydrogenation, and irradiation described by Greene, *Protective Groups in Organic Synthesis*, Wiley-Interscience, (1980).

Scheme V

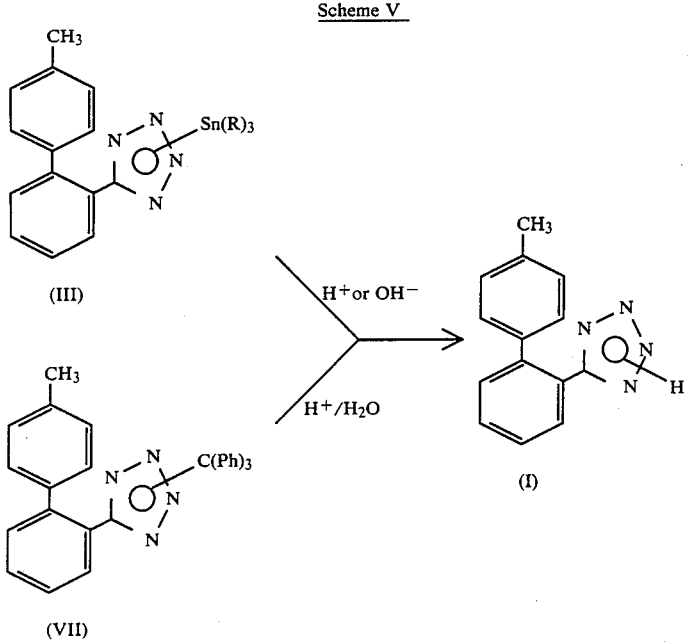

Compounds of the Formula (I) where $X^1$ is C(phenyl)$_3$ and $X^2$ is Br may be prepared via radical bromination of (VII) with N-bromosuccinimide (NBS) and dibenzoylperoxide (Bz$_2$O$_2$) to yield (XII) as shown in Scheme VI. An example of this conversion is described by L. Horner et al., *Angew. Chem.*, 71, 349 (1959).

Scheme VI

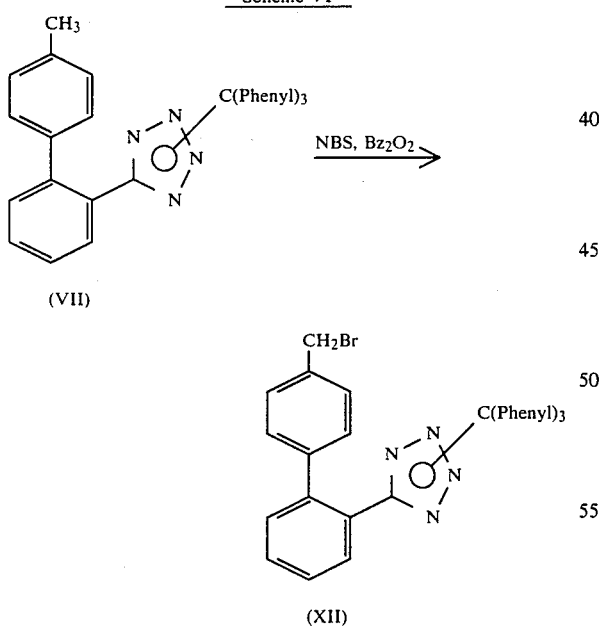

Compounds of the Formula (I) where $X^1$ is C(Phenyl)$_3$ and $X^2$ is I may be prepared via displacement of the bromine moiety in (XII) with sodium iodide in acetone under standard conditions yielding (XIII). Displacement of the above bromide (XII) with hydroxide ion affords the substituted benzyl alcohol (XIV). The benzyl alcohol (XIV) may be converted to the chloride (XV) via reaction with carbon tetrachloride and triphenylphosphine. The benzyl alcohol (XIV) can be converted to the tosylate or mesylate (XVI) via reaction with p-toluenesulfonyl chloride or methanesulfonyl chloride, respectively, in pyridine under standard conditions (Scheme VII).

Scheme VII

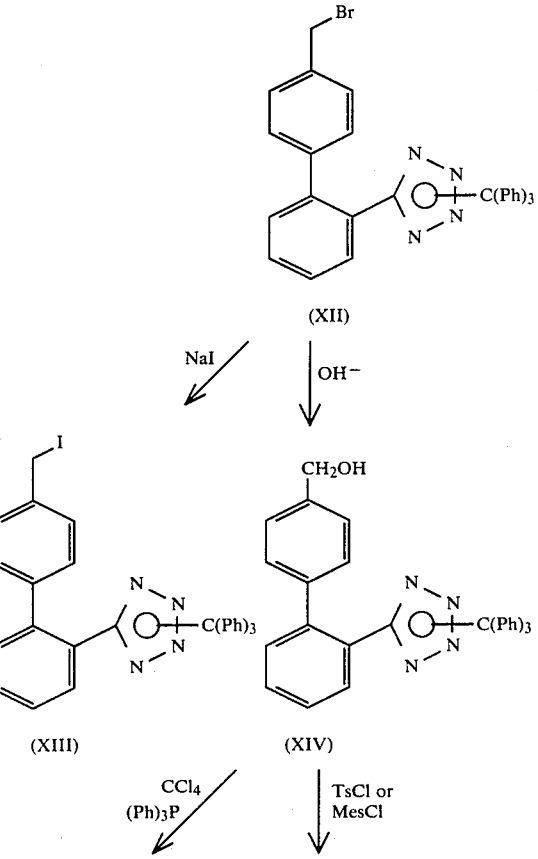

11
-continued
Scheme VII

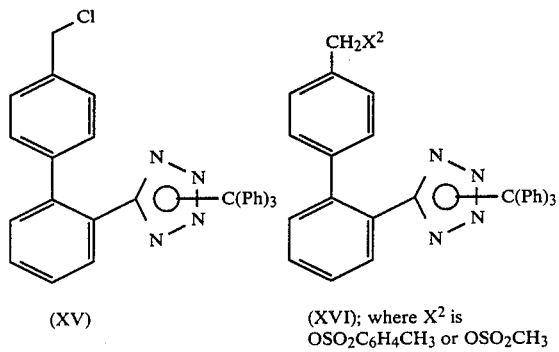

(XV)

(XVI); where $X^2$ is $OSO_2C_6H_4CH_3$ or $OSO_2CH_3$

Compounds of the Formula (I) where $X^1$ is $C(Phenyl)_3$ and $X^2$ is imidazoyl where $R^1$ is n-butyl, $R^3$ is Cl, and $R^2$ is hydroxymethyl may be prepared via alkylation of imidazole (XVII) with the appropriately substituted benzyl halide using sodium ethoxide as a base followed by reduction of the formaldehyde moiety on imidazole (XVII) to hydroxymethyl with sodium borohydride affording (XVIII). The preparation of imidazole (XVII) in Scheme VIII is described by Furukawa, et al. in U.S. Pat. No. 4,355,040.

Scheme VIII

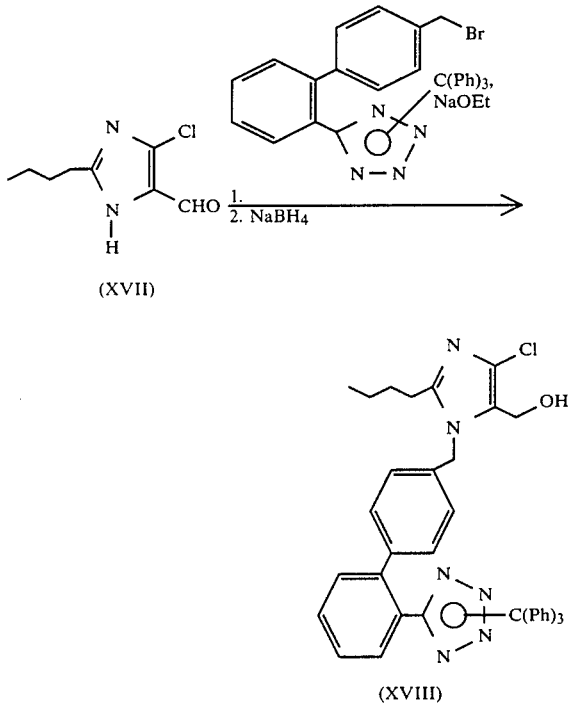

The compounds of this invention and their preparation can be understood further by the following examples, but should not constitute a limitation thereof. In these examples, unless otherwise indicated, all temperatures are in degrees centrigrade and parts and percentages are by weight.

12
EXAMPLE 1
Method A

Part A:
N-trimethylstannyl-5-[2-(4'-methylbiphen-2-yl)]tetrazole

To a solution of 2-cyano-4'-methylbiphenyl (19.30 g, 0.100 mole) in toluene (110.0 ml) was added trimethyltin azide (24.60 g, 0.120 mole) at room temperature. The reaction was refluxed for 24 hours, cooled to room temperature and the product isolated by filtration affording N-trimethylstannyl-5-[2-(4'-methylbiphenylyl)-]tetrazole (32.60 g, 82%) as an off white solid, m.p. 265° (dec.); $^1$H NMR (DMSO-d$_6$) δ: 7.50 (s, 4H); 7.00 (s, 4H); 2.25 (s, 3H); 0.35 (s, 3H).

Part B: 5-[2-(4'-methylbiphenylyl)]tetrazole

To a solution of N-trimethylstannyl-5-[2-(4'-methyl-biphenylyl)]tetrazole (32.0 g, 0.080 mole) in toluene (230 ml) and tetrahydrofuran (15.0 ml) was bubbled in enough anhydrous hydrogen chloride to give a clear solution at room temperature. From this solution, 5-[2-(4'-methylbiphenylyl)]tetrazole (19.1 g) crystallized. Recrystallization from toluene afforded 18.1 g (95%) of product, m.p. 149°–152°. $^1$H NMR (CDCl$_3$/DMSO-d$_6$) δ: 7.50 (m, 4H); 7.07 (m, 4H); 2.35 (s, 3H).

EXAMPLE 1
Method B

Part A: 4'-Methyl-biphenyl-2-carbonyl chloride

A solution of 4'-methyl-biphenyl-2-carboxylic acid (31.84 g, 0.15 mole) in chloroform (200 ml) was added dropwise to a stirred mixture of chloroform (25 ml) oxalyl chloride (25 ml), and dimethylformamide (1.0 ml) at room temperature. After the mixture had stirred for 24 hours at room temperature, the solution was evaporated in vacuo affording 36.4 grams of the crude acid chloride. IR: 1784.0 cm$^{-1}$(COCl).

Part B:
N-(4-Nitrobenzyl)-4'-methyl-biphenyl-2-carboxamide

A solution of the material from Part A (36.4 g) in dry acetonitrile was added dropwise to a cooled (ice-bath), stirred mixture of 4-nitrobenzylamine hydrochloride (23.45 g, 0.12 mole), 4-dimethylamino pyridine (0.5 g, 0.0041 mole), and dry pyridine (150.0 ml). After 30 minutes, the reaction was allowed to reach room temperature and stirred for 16 hours at room temperature. The mixture was poured into a stirred mixture of 3N HCl (800.0 ml), ice (400.0 g), and dichloromethane (400 ml). The organic layer was washed with 2N NaOH (2×200 ml), brine (100 ml), dried (MgSO$_4$), and evaporated in vacuo to yield crude product (61.9 g). Recrystallization from ethyl acetate gave 31.3 (73%) of product, m.p. 153°–154°. $^1$H NMR (CDCl$_3$) δ: 8.03 (d, 2H, aromatic); 7.65–7.69 (m, 1H, aromatic); 7.12–7.48 (m, 7H, aromatic); 7.04 (d, 2H, aromatic); 5.77–5.79 (m, 1H, NH); 4.41 (d, 2H, J=6.0 Hz, CH$_2$); 2.39 (s, 3H, CH$_3$). Mass spec m/z=347 (M+1).

Part C:
N-(4-Nitrobenzyl)-4'-methyl-biphen-2-ylcarboiminoyl chloride

In three portions, a total of 20.78 g (0.060 mole) of the product of Part B was added to a cooled (ice-bath), stirred solution of phosphorus pentachloride (12.49 g, 0.066 mole) in carbon tetrachloride (200 ml). The mixture was stirred for 30 minutes at 0°, allowed to warm to room temperature, and stirred for 16 hours. The mixture was evaporated in vacuo yielding the crude product (21.3 g). IR: 1691 cm$^{-1}$ (C=N). $^1$H NMR (CDCl$_3$) δ: 4.79 (s, 2H, CH$_2$).

Part D:
1-(4-Nitrobenzyl)-5-(4'-methyl-biphen-2-yl)tetrazole

Lithium azide (3.67 g, 0.75 mole) was added portionwise to a cooled solution (ice-bath) of the product of Part C (21.3 g) in dimethylformamide (200.0 ml). The mixture was allowed to reach room temperature over 16 hrs. The reaction mixture was evaporated in vacuo. The residue was partitioned between water and ethyl acetate (100 ml). The organic layer was washed with water (100 ml), dried (MgSO$_4$) and evaporated in vacuo to yield 19.5 g of a dark residue. Chromatography on silica (CHCl$_3$) followed by recrystallization (methanol) afforded 5.37 g, (24.1%), m.p. 95.0°–96.0°. $^1$H NMR (CDCl$_3$) δ: 7.98–8.02 (m, 2H, aromatic); 7.55–7.70 (m, 2H, aromatic); 7.37–7.49 (m, 2H, aromatic); 6.99–7.10 (m, 2H, aromatic); 4.87 (d, J=8.7 Hz, aromatic); 4.88 (s, 2H, CH$_2$); 2.33 (s, 3H, CH$_3$). Mass spec m/z=372 (M+1).

Part E: 5-[2-(4'-methylbiphen-2-yl)]tetrazole

A mixture of the product of Part D (1.00 g, 2.80 mmole), ethanol (150.0 ml), and W6 Raney nickel (5.0 g) was hydrogenated in a Parr ® Shaker at 50 psi for 2 hrs. at room temperature. The catalyst was removed by filtration, and the filtrate was evaporated in vacuo. The residue was partitioned between water and diethyl ether (100 ml) and the organic layer was washed with 1N HCl (50 ml), brine (50 ml), dried (MgSO$_4$), and evaporated in vacuo to yield a solid residue which was recrystallized from toluene to yield the product (0.19 g, 28.7%), m.p. 154°–155°. $^1$H NMR (CDCl$_3$) δ; 11.5 (br s, 1H, NH); 8.02 (d, 1H, aromatic); 7.38–7.61 (m, 3H, aromatic), 7.16 (d, 2H, J=8.0 Hz, aromatic); 7.04 (d, 2H, J=8.0 Hz); 2.35 (s, 3H, CH$_3$). Mass spec m/z=237 (M+1).

EXAMPLE 1

Method C

Part A:
2-(α-cyanoethylaminocarbonyl)-4'-methylbiphenyl

4'-methylbiphenyl-2-carboxylic acid (50.00 g, 0.236 mol,), thionyl chloride (87.5 ml, 1.20 mol) and chloroform (500 ml) were mixed and refluxed for 4 hours. The thionyl chloride and solvent were removed in vacuo, and the residue suspended in toluene (300 ml). The mixture was evaporated in vacuo and the residue suspended once more in toluene and evaporated to insure removal of traces of thionyl chloride. The resultant acid chloride was dissolved in tetrahydrofuran (100 ml) and slowly added in five equal portions alternatingly with five equal portions of 1,0N NaOH (236.0 ml, 0.236 mol) to a solution of β-aminopropionitrile fumarate (30.3 g, 0.236 mol) in 1,0N NaOH (236.0 ml, 0.236 mol) at 0° with stirring. The reaction was allowed to warm slowly to room temperature. After 24 hrs, water (500 ml) was added and the aqueous mixture extracted with ethyl acetate (3×500 ml). The organic layers were combined and dried (MgSO$_4$), and the solvent removed in vacuo to yield a crude solid which, after recrystallization from methylcyclohexane/butyl chloride, yielded 53.5 g of a white solid. M.P.=102.0°–103.5°. NMR (200MH$_2$, CDCl$_3$) δ: 7.68 (d, 1H, J=7H$_z$); 7.56–7.19 (m, 7H); 5.65 (bm, 1H); 3.43 (d of t, 2H); 2.39 (t, 2H, J=7H$_z$). Anal. calcd. for C$_{17}$H$_{16}$N$_2$O; C, 77.25; H, 6.10; N, 10.60. Found; C, 77.42; H, 6.40; N, 10.68.

Part B:
N$^3$-(β-cyanoethyl)-4'-methylbiphenyl-2-yl-amidrazone 2-(β-cyanoethylaminocarbonyl)-4'-methylbiphenyl (33.48 g, 0.127 mol) and phosphorous pentachloride (29.01 g, 0.139 mol) were combined in a round bottom flask which was then connected to aspirator vacuum via a trap filled with calcium chloride. The flask was gently heated with a heat gun until the solids melted. The flask was intermittantly heated for 15–20 minutes.

The crude iminoyl chloride was taken up in dry dioxane (100 mL) and added dropwise to a stirred mixture of hydrazine (20.1 mL, 0.634 mol) in dry dioxane (200 mL). After 24 hours, the excess hydrazine and solvent were removed in vacuo. Water (300 mL) was added, and the aqueous mixture extracted with ethyl acetate (3×300 mL). The organic layers were combined, dried (MgSO$_4$) and the solvent removed in vacuo to yield an oil. The oil was treated with a 1:1 hexane/ethyl acetate solution (30–50 mL), and solids precipitated. These were collected and dried to yield 16.14 g of light pink solids. M.P.=146.5°–147.5°. Chemical ionization mass spectrum detected (M+H)$^+$=279 for C$_{17}$H$_{19}$N$_4$. Anal. calcl. for C$_{17}$H$_{18}$N$_4$.(N$_2$H$_4$)$_{0.1}$: C, 72.52; H, 6.44; N, 20.89. Found: C, 72.50; H, 6.54; N, 21.13. NMR indicated a mixture of tautomeric forms.

Part C:
2-[1-(β-cyanoethyl)-1-H-tetrazol-5-yl]-4'-methylbiphenyl

A solution of N$_2$O$_4$(g) in carbon tetrachloride (0.73M, 19.6 mL, 14.3 mmol) was added to a stirred slurry of N$^3$-(β-cyanoethyl)-4'-methylbiphenyl-2-ylamidrazone (2.00 g, 7.2 mmol) in anhydrous acetonitrile (40 mL) at 0°. The reaction was warmed to room temperature and stirred overnight. The solvent was removed in vacuo to yield a crude solid. This solid was taken up in butyl chloride and the insoluble matter filtered. The filtrate was evaporated, and the residue flash chromatographed on silica in 1:1 hexane/ethylacetate to yield 1.10 g of a pale yellow oil, which slowly crystallized. Recrystallization from hexane/butyl chloride yielded 910 mg of pale yellow crystals. M.P.=90.0°–92.0°. NMR(200 MH$_z$, CDCl$_3$) δ: 7.76–7.50 (m, 4H); 7.17(d, 2H, J=10H$_z$); 7.04(d, 2H, J=10H$_z$); 3.80 (t, 2H, J=7H$_z$); 2.37 (s, 3H); 2.24(bt, 2H, J=7H$_z$). Anal. calcd. for C$_{17}$H$_{15}$N$_5$: C, 70.57; H, 5.23; N, 24.20. Found: C, 70.49; H, 5.45; N, 24.44.

Part D: 5-(4'-methylbiphenyl-2-yl)tetrazole

2-[1-(β-cyanoethyl)-1-H-tetrazol-5-yl]-4'-methylbiphenyl (689 mg, 2.38 mmol), 1,0N NaOH (2.62 mL, 2.62 mmol) and THF (15 mL) were mixed and stirred at room temperature. After 15 minutes, water (100 mL) was added and the pH adjusted to 3.0 with conc. HCl. The aqueous mixture was extracted with ethyl acetate (3×100 mL) and the organic layers were combined, dried (MgSO$_4$) and evaporated in vacuo to yield 550 mg of a white powder. M.P.=148.5°–150.0°. The spectral data matched those of a sample prepared via Method A.

EXAMPLE 5

N-triphenylmethyl-5-[2-(4'-methylbiphenylyl)tetrazole

To a solution of 5-[2-(4'-methylbiphenlyl)]tetrazole (17.0 g, 0.072 mole) in methylene chloride (260 ml) was added triphenylmethyl chloride (21.20 g, 0.076 mole) at room temperature. Triethylamine (12.0 ml, 0.086 mole) was added at room temperature, and the solution was refluxed for 2.5 hrs. The solution was cooled to room temperature, washed with water (2×50 ml), dried (MgSO₄), and evaporated in vacuo. The residue was crystallized from toluene (80 ml), yielding, N-triphenylmethyl-5-[2-(4'-methylbiphenylyl)]tetrazole (31.2 g, 90%), m.p. 163°–166°; $^1$H NMR (CDCl₃) δ: 8.10–6.80 (complex, 23H); 2.28 (s, 3H).

EXAMPLE 6

N-triphenylmethyl-5-[2-(4'-bromomethyl-biphenylyl)-]tetrazole

To a solution of N-triphenylmethyl-5-[2-(4'-methylbiphenylyl)]tetrazole (31.0 g, 0.065 mole) in carbon tetrachloride (390.0 ml) was added N-bromosuccinimide (11.50 g, 0.065 mole) and dibenzoylperoxide (1.10 g, 0.0045 mole) at room temperature. The reaction mixture was refluxed for 3 hrs., cooled to 40° and filtered. Evaporation of the filtrate in vacuo followed by trituration of the residue with isopropyl ether (100.0 ml) yielded N-triphenylmethyl-5-[2-(4'-bromomethyl-biphenylyl)]tetrazole (33.10 g, 92%), m.p. 135°–138°. $^1$H NMR (CDCl₃) δ: 8.20–6.70 (complex, 23H); 4.33 (s, 2H).

EXAMPLE 7

1-{[2'-(N-triphenylmethyl-tetrazol-5-yl)-biphenyl-4-yl]methyl}-2-butyl-4-chloro-5-hydroxymethyl imidazole To a solution of 2-butyl-4-chloro-5-formylimidazole (1.24 g, 0.007 mole) dissolved in dimethylformamide (10.0 ml) was added sodium ethoxide (0.45 g, 0.0066 mole) and the reaction mixture was cooled to 5°. N-triphenylmethyl-5-[2-(4'-bromomethylbiphenylyl]tetrazole (3.70 g, 0.0066 mole) was added and the reaction mixture was allowed to warm to room temperature. After 72 hrs. the reaction was diluted with water (25.0 ml) and extracted with ethyl acetate (3×25 ml). The organic phase was washed with water (2×25 ml) and brine (3×25 ml), dried (MgSO₄), and evaporated in vacuo to an oil. The crude oil was dissolved in methanol (20.0 ml), and sodium borohydride (0.24 g, 0.0063 mole) was added at room temperature. The reaction was stirred for 1.5 hrs., diluted with water (40.0 ml), and extracted with ethyl acetate (2×50 ml). The organic layer was washed with water (1×25 ml), dried (MgSO₄), and evaporated in vacuo. The residue was recrystallized once from toluene/heptane, once from toluene, and finally from methanol to give 1-{[2'-(N-triphenylmethyl-tetrazol-5-yl)-biphenyl-4-yl]methyl}-2-butyl-4-chloro-5-hydroxymethyl imidazole (0.98 g, 21%), m.p. 95°–98°; $^1$H NMR (CDCl₃) δ: 8.20–6.60 (complex, 23H); 5.16 (s, 3H); 4.40 (s, 3H); 2.85 (brs, 1H); 2.54 (t, 3H); 1.9–1.1 (m, 4H); 0.88 (t, 3H).

EXAMPLE 8

1-{[2'-(N-trimethylstannyl-tetrazol-5-yl)-biphenyl-4-yl]methyl}-2-butyl-4-chloro-5-hydroxymethyl imidazole To a solution of 1-[(2'-cyano-biphenyl-4-yl)methyl]-2-butyl-4-chloro-5-hydroxymethyl-imidazole (4.40 g, 0.011 mole) in xylenes (40.0 ml) was added trimethyltin azide (2.80 g, 0.014 mole), and the reaction was heated at 115°–120° for 40 hrs. The mixture was cooled to 50° and filtered to yield 1-{[2'-(N-trimethylstannyl-tetrazol-5-yl)-biphenyl-4-yl]methyl}-2-butyl-4-chloro-5-hydroxymethyl imidazole (6.55 g, 99%), m.p. 154°–160°; $^1$H NMR (CDCl₃/DMSO-d₆) δ: 7.80–7.30 (m, 4H), 7.03 (q, 4H), 5.23 (s, 3H), 4.43 (s, 3H), 2.54 (t, 3H); 2.00 (s, 1H), 1.80–1.10 (m, 4H); 0.85 (t, 3H); 0.40 (s, 9H).

The compounds of Examples 1, 5, 6, 7, and 8 above as well as other compounds which were prepared or could be prepared using the procedures of the aforementioned examples are shown in Table I.

TABLE I

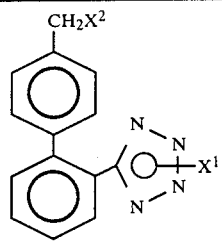

| Ex. | $X^1$ | $X^2$ | Method | $R^1$ | $R^2$ | $R^3$ | M.P. °C. |
|---|---|---|---|---|---|---|---|
| 1 | H | H | A, B, C | — | — | — | 149–155 |
| 1D | P—NO₂benzyl | H | B | — | — | — | 95–96 |
| 2 | Sn(Ph)₃ | H | A | — | — | — | 204–209 |
| 3 | Sn(n-Pr)₃ | H | A | — | — | — | — |
| 4 | Sn(c-C₆H₁₁)₃ | H | A | — | — | — | — |
| 5 | C(Phenyl)₃ | H | — | — | — | — | 163–166 |
| 6 | C(Phenyl)₃ | Br | — | — | — | — | 135–138 |
| 7 | C(Phenyl)₃ | Im | — | n-Bu | CH₂OH | Cl | 95–98 |
| 8 | Sn(CH₃)₃ | Im | A | n-Bu | CH₂OH | Cl | 154–160 |
| 9 | Sn(Ph)₃ | Im | A | n-Bu | CH₂OH | Cl | |
| 10 | Sn(n-Bu)₃ | Im | A | n-Bu | CH₂OH | Cl | |
| 11 | H | OH | — | — | — | — | |
| 12 | C(Phenyl)₃ | Cl | — | — | — | — | |
| 13 | Sn(CH₃)₃ | Im | A | n-Pr | CH₂OH | Cl | |
| 14 | Sn(Ph)₃ | Im | A | n-Pr | CH₂OH | Cl | |
| 15 | Sn(n-Bu)₃ | Im | A | n-Pr | CH₂OH | Cl | |
| 16 | C(Phenyl)₃ | Im | — | n-Pr | CH₂OH | Cl | |

TABLE I-continued

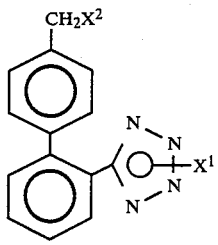

| Ex. | X¹ | X² | Method | R¹ | R² | R³ | M.P. °C. |
|---|---|---|---|---|---|---|---|
| 17 | p-NO$_2$C$_6$H$_4$CH$_2$ | Im | B | n-Bu | CH$_2$OH | Cl | |
| 18 | Sn(CH$_3$)$_3$ | Im | A | n-Bu | CHO | Cl | |
| 19 | C(Phenyl)$_3$ | Im | — | n-Bu | CHO | H | |
| 20 | Sn(CH$_3$)$_3$ | Im | A | n-Bu | CH$_2$NHCO$_2$CH$_3$ | Cl | |
| 21 | Sn(CH$_3$)$_3$ | Im | A | n-Bu | CH$_2$NHSO$_2$CH$_3$ | Cl | |
| 22 | C(Phenyl)$_3$ | Im | — | n-Bu | (CH$_2$)$_3$O—C(=O)—CH$_3$ | Cl | |
| 23 | Sn(CH$_3$)$_3$ | Im | A | n-Bu | CH$_2$NHSO$_2$CF$_3$ | Cl | |
| 24 | C(Phenyl)$_3$ | Im | A | n-Bu | CH$_2$NHSO$_2$CF$_3$ | Cl | |
| 25 | Sn(CH$_3$)$_3$ | Im | A | n-Bu | CH$_2$OH | H | |
| 26 | C(Ph)$_3$ | Im | — | n-Bu | CH$_2$OH | H | |
| 27 | Sn(CH$_3$)$_3$ | Im | A | n-Bu | CHO | H | |
| 28 | C(Ph)$_3$ | Im | — | n-Bu | CHO | H | |
| 29 | Sn(CH$_3$)$_3$ | Im | A | —CH=CHCH$_3$ | CH$_2$OH | Cl | |
| 30 | C(Ph)$_3$ | Im | — | —CH=CHCH$_3$ | CH$_2$OH | Cl | |
| 31 | Sn(CH$_3$)$_3$ | Im | A | —C≡C—CH$_3$ | CH$_2$OH | Cl | |
| 32 | C(Ph)$_3$ | Im | — | —C≡C—CH$_3$ | CH$_2$OH | Cl | |
| 33 | CH$_2$CH$_2$CN | Im | C | n-Bu | CH$_2$OH | Cl | |
| 34 | C(Phenyl)$_3$ | I | — | — | — | — | |
| 35 | C(Phenyl)$_3$ | OTs | — | — | — | — | |
| 36 | C(Phenyl)$_3$ | OMes | — | — | — | — | |
| 37 | Sn(CH$_3$)$_3$ | OH | A | — | — | — | |
| 38 | Sn(Ph)$_3$ | OH | A | — | — | — | |
| 39 | Sn(c-C$_6$H$_{11}$)$_3$ | OH | A | — | — | — | |

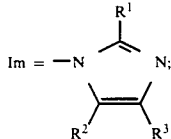

Im =

What is claimed is:

1. A tetrazole having the formula:

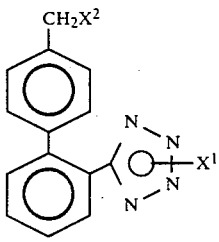

(I)

wherein

X¹ is H, —C(Phenyl)$_3$, p-nitrobenzyl, or β-propionitrile,

X² is

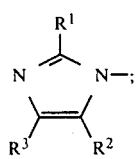

R¹ is alkyl of 3–10 carbon atoms, alkenyl of 3 to 10 carbon atoms, alkenyl of 3 to 10 carbon atoms, alkynyl of 3 to 10 carbon atoms, and benzyl substituted with up to two groups selected from alkoxy of 1 to 4 carbon atoms, halogen, alkyl of 1 to 4 carbon atoms, nitro and amino;

R² is

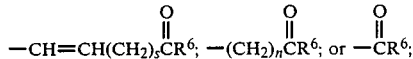

R³ is H, F, Cl, Br, I, NO$_2$, CF$_3$, or CN;

R⁶ is NR$^{10}$R$^{11}$;

R$^{10}$ and R$^{11}$ taken together to form a ring of the Formula

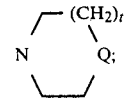

Q is NR$^{12}$, O or CH$_2$;

R$^{12}$ is H, alkyl of 1 to 4 carbon atoms, or phenyl;

n is 1 to 10;

s is 0 to 5;

t is 0;

with the proviso that when $X^1$=H then $X^2$ cannot be

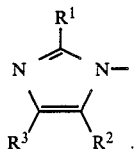

2. The tetrazole of claim 1 wherein $X^1$ is H, or —C(-Phenyl)$_3$.

3. The tetrazole of claim 1 wherein
$R^1$ is alkyl, alkenyl or alkynyl of 3 to 7 carbon atoms;
$R^2$ is

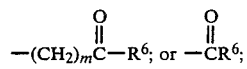

$R^3$ is H, Cl, Br, or I; and
m is 1 to 5.

4. The tetrazole of claim 2 wherein
$R^1$ is alkyl, alkenyl or alkynyl of 3 to 7 carbon atoms;
$R^2$ is

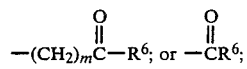

$R^3$ is H, Cl, Br, or I; and
m is 1 to 5.

5. The tetrazole of claim 4 wherein
$R^1$ is alkyl of 3 to 7 carbon atoms; and
$R^3$ is Cl.

* * * * *